(12) United States Patent
Latini et al.

(10) Patent No.: US 10,557,858 B2
(45) Date of Patent: Feb. 11, 2020

(54) BIOMARKERS FOR RISK PREDICTION OF MORTALITY

(71) Applicant: Roche Diagnostics Operations, Inc., Indianapolis, IN (US)

(72) Inventors: Roberto Latini, Milan (IT); Serge Masson, Monza (IT); Dirk Block, Bichl (DE); Christian Zaugg, Rheinfelden (CH); Thomas Dieterle, Freiburg (DE); Edelgard Kaiser, Hünenberg See (CH); Johann Karl, Peissenberg (DE); Vinzent Rolny, Munich (DE); Ursula-Henrike Wienhues-Thelen, Krailling (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/581,587

(22) Filed: Apr. 28, 2017

(65) Prior Publication Data

US 2017/0227552 A1 Aug. 10, 2017

Related U.S. Application Data

(63) Continuation of application No. PCT/EP2015/075012, filed on Oct. 28, 2015.

(30) Foreign Application Priority Data

Oct. 29, 2014 (EP) .................................... 14190836
Nov. 11, 2014 (EP) .................................... 14192653

(51) Int. Cl.
*G01N 33/50* (2006.01)
*G01N 33/68* (2006.01)

(52) U.S. Cl.
CPC . *G01N 33/6893* (2013.01); *G01N 2333/4703* (2013.01); *G01N 2333/58* (2013.01); *G01N 2800/325* (2013.01)

(58) Field of Classification Search
None
See application file for complete search history.

(56) References Cited

U.S. PATENT DOCUMENTS

| 2007/0248981 | A1 | 10/2007 | Snider et al. | |
| 2009/0326053 | A1* | 12/2009 | Walsh | C12Q 1/6883 514/44 R |
| 2010/0255520 | A1 | 10/2010 | Kavsak | |
| 2015/0185230 | A1* | 7/2015 | Block | G01N 33/6887 435/7.94 |

FOREIGN PATENT DOCUMENTS

| CN | 103487586 | | 1/2014 | |
| WO | 1999/006445 A1 | | 2/1999 | |
| WO | 2000/070051 A1 | | 11/2000 | |
| WO | 2005/113585 A2 | | 12/2005 | |
| WO | WO 2008/089994 | * | 7/2008 | ............ G01N 33/68 |
| WO | 2012/025355 A1 | | 3/2012 | |
| WO | 2012/106152 A1 | | 8/2012 | |
| WO | 2014/040759 A1 | | 3/2014 | |
| WO | 2015/144767 A1 | | 10/2015 | |

OTHER PUBLICATIONS

Hammerer-Lercher et al., Analysis of Circulating Forms of proBNP and NT-proBNP in Patients with Severe Heart Failure, Clin. Chem., (2008), 54(5), p. 858-865.*
Qi et al., Effects of different peptide fragments derived from proadrenomedullin on gene expression of adrenomedullin gene, Peptides, (2002), 23, p. 1141-1147.*
Masson et al., High-sensitivity cardiac troponin T for detection of subtle abnormalites of cardiac phenotype in a general population of elderly individuals, Journal of Internal Medicine, Mar. 2013, Issue 3, 273, pp. 306-317.*
Weinberg et al., Expression and regulation of ST2, an Interleukin-1 receptor family member, in cardiomyocytes and myocardial infarction, Circulation, 2002:106,j pp. 2961-2966. (Year: 2002).*
Yeong et al., Plasma Angiopoietin-1, Angiopoietin-2, and Angiopoietin Receptor Ti2 levels in Congestive Heart Failure, Journal of the American College of Cardiology, vol. 43, No. 3, 2004, pp. 423-428. (Year: 2004).*
Tousoulis et al., Increased plasma adhsion molecule levels in patients with heart failure who have ischmic heart disease and dilated cardiomyopathy, American Heart Journal, Feb. 2001, pp. 277-280. (Year: 2001).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Anderson, Page A. W. et al., Molecular Basis of Human Cardiac Troponin T Isoforms Expressed in the Developing, Adult, and Failing Heart, Circulation Research, 1995, pp. 681-686, vol. 76.
Angheloiu, George O. et al, Etiology of troponin I elevation in patients with congestive heart failure and low clinical suspicion of myocardial infarction, Resuscitation, 2004, pp. 195-201, vol. 63.

(Continued)

Primary Examiner — Gary Counts
(74) Attorney, Agent, or Firm — Roche Diagnostics Operations, Inc.

(57) ABSTRACT

Described is a method for predicting the risk of a subject of rapidly progressing to chronic heart failure and/or of hospitalization due to chronic heart failure and/or death. The method is based on the determination of at least one biomarker selected from B-type natriuretic peptide (BNP) or N-terminal pro B-type natriuretic peptide (NT-proBNP), IGFBP7 (IGF binding protein 7), a cardiac Troponin, soluble ST2 (sST2), FGF-23 (Fibroblast Growth Factor 23), and Growth Differentiation Factor 15 (GDF-15), in a sample of a subject along with the assessment of the presence or absence of (i) abnormal midwall fractional shortening or (ii) left ventricular hypertrophy.

23 Claims, 12 Drawing Sheets

(56) References Cited

OTHER PUBLICATIONS

Baek, Seung Joon et al., Cyclooxygenase Inhibitors Regulate the Expression of a TGF-β Superfamily Member That Has Proapoptotic and Antitumorigenic Activities, Molecular Pharmacology, 2001, pp. 901-908, vol. 59, No. 4.

Bootcov, Michelle R. et al., MIC-1, a novel macrophase inhibitory cytokine, is a divergent member of the TGF-β superfamily, Proceedings of the National Academy of Sciences USA, 1997, pp. 11514-11519, vol. 94.

Böttner, Martina et al., Characterization of the rat, mouse, and human genes of growth/differentiation factor-15/macrophage inhibiting cytokine-1 (GDF-15/MIC-1), Gene, 1999, pp. 105-111, vol. 237.

De Lemos, James A. et al., Screening the population for left ventricular hypertrophy and left ventricular systolic dysfunction using natriuretic peptides: Results from the Dallas Heart Study, American Heart Journal, 2009, pp. 746-753, el-e2, vol. 157.

De Simone, Giovanni et al., Assessment of Left Ventricular Function by the Midwall Fractional Shortening/End-Systolic Stress Relation in Human Hypertension, Journal of the American College of Cardiology, May 1994, 1444-1451, vol. 23, No. 6.

Dieplinger, Benjamin et al., Long-term stability of soluble ST2 in frozen plasma samples, Clinical Biochemistry, 2010, pp. 1169-1170, vol. 43.

Drazner, Mark H. et al., Left Ventricular Hypertrophy Is More Prevalent in Blacks Than Whites in the General Population the Dallas Heart Study, Hypertension, 2005, pp. 124-129, vol. 46.

Ferrieres, Gaelle et al., Human cardiac troponin I: precise identification of antigenic epitopes and prediction of secondary structure, Clinical Chemistry, 1998, pp. 487-493, vol. 44, No. 3.

Frohlich, Edward D. et al., Hyprtensive left ventricular hypertrophy risk: beyond adaptive cardiomyocytic hypertrophy, Journal of Hypertension, 2011, pp. 17-26, vol. 29.

Gerok, Wolfgang et al., Die Innere Medizin: Referenzwerk für den Facharzt, 2007, 293-294, Schattauer.

Goicoechea, Marian et al., Clinical Significance of Cardiac Troponin T Levels in Chronic Kidney Disease Patients: Predictive Value for Cardiovascular Risk, American Journal of Kidney Diseases, 2004, pp. 846-853, vol. 43, No. 5.

Hromas, Robert et al., PLAB, a novel placental bone morphogenetic protein, Biochimica et Biophysica Acta, 1997, pp. 40-44, vol. 1354.

Hunt, Sharon Ann et al., ACC/AGA 2005 Guideline Update for the Diagnosis and Management of Chronic Heart Failure in the Adult, Journal of the American College of Cardiology, 2005, pp. e1-e82, vol. 46.

International Search Report dated Mar. 17, 2016 in Application No. PCT/EP2015/075012, p. 1-25.

Ishii, Junnichi et al., Risk Stratification Using a Combination of Cardiac Troponin T and Brain Natriuretic Peptide in Patients Hospitalized for Worsening Chronic Heart Failure, American Journal of Cardiology, 2002, pp. 691-695, vol. 89.

Lawton, Lee N. et al., Identification of a novel member of the TGF-beta superfamily highly expressed in human placenta, Gene, 1997, pp. 17-26, vol. 203.

Levey, Andrew S. et al., A More Accurate Method to Estimate Glomerular Filtration Rate from Serum Creatinine: A Prediction Equation, Annals of Internal Medicine, 1999, pp. 461-470, vol. 130, No. 6.

Mancia, Giuseppe et al., 2007 Guidelines for the management of arterial hypertension, European Heart Journal, 2007, pp. 1462-1536, vol. 28.

Masson, Serge et al., Abstract 12358: Abnormal Left Ventricular Midwall Fractinal Shortening and Elevated Circulating Biomarkers Predict High Mortality in Elderly Individuals in the General Population, Circulation, 2014, Supplement 1, A12358, vol. 130 (Supp 2).

Mayet, Jamil et al., Improvement in Midwall Myocardial Shortening With Regression of Left Ventricular Hypertrophy, Hypertension, 2000, pp. 755-759, vol. 34.

McMurray, John J. V. et al., ESC Guidelines for the diagnosis and treatment of acute and chronic heart failure 2012, European Heart Journal, 2012, pp. 1787-1847, vol. 33.

Miller, Wayne L. et al., Only Large Changes (> 80%) in BNP Modify Risk in Patients with Chronic Heart Failure, Journal of Cardiac Failure, 2007, p. S105, vol. 13.

Morrish, D. W. et al., Identification by Subtractive Hybridization of a Spectrum of Novel and Unexpected Genes Associated with In Vitro Differentiation of Human Cytotrophoblast Cells, Placenta, 1996, pp. 431-441, vol. 17.

Mureddu, Gian Francesco et al., Prevalence of preclinical and clinical heart failure in the elderly. A population-based study in Central Italy, European Journal of Heart Failure, 2012, pp. 718-729, vol. 14, No. 7.

Needland, Ian J. et al., Biomarkers of Chronic Cardiac Injury and Hemodynamic Stress Identify a Malignant Phenotype of Left Ventricular Hypertrophy in the General Population, Journal of the American College of Cardiology, 2013, pp. 187-195, vol. 61, No. 2.

Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.

Paralkar, Vishwas M. et al., Cloning and Characterization of a Novel Member of the Transforming Growth Factor-β/Bone Morphogenetic Protein Family, The Journal of Biological Chemistry, 1998, pp. 13760-13767, vol. 273, No. 22.

Satyan, Sangeetha et al., Relationships of N-Terminal Pro-B-Natriuretic Peptide and Cardiac Troponin T to Left Ventricular Mass and Function and Mortality in Asymptomatic Hemodialysis Patients, American Journal of Kidney Diseases, 2007, pp. 1009-1019, vol. 50, No. 6.

Shimada, Takashi et al., Cloning and characterization of FGF23 as a causative factor of tumor-induced osteomalacia, PNAS, 2001, pp. 6500-6505, vol. 98, No. 11.

Shimizu, Gen et al., Left Ventricular Midwall Mechanics in Systemic Arterial Hypertension Myocardial Function is Depressed in Pressure-Overload Hypertrophy, Circulation, 1991, pp. 1676-1684, vol. 83.

Shimizu, Gen et al., Phase-plane analysis of left ventricular chamber filling and midwall fiber lengthening in patients with left ventricular hypertrophy, Circulation, 1987, pp. I-34-I-39, Supplement I.

Shmizu, Gen et al., Left ventricular chamber filling and midwall fiber lengthening in patients with left ventricular hypertrophy: overestimation of fiber velocities by conventional midwall measurements, Circulation, 1985, pp. 266-272, vol. 71, No. 2.

Shroff, Rukshana C. et al., Circulating Angiopoietin-2 Is a Marker for Early Cardiovascular Disease in Children on Chronic Dialysis, PLoS One, 2013, e56273, 10 pps, vol. 8, No. 2.

Swamy, Rajiv S. and Long, Roberto M., Echocardiographic Quantification of Left Ventricular Mass: Prognostic Implications, Current Cardiology Reports, 2010, pp. 277-282, vol. 12.

Tan, Mingjia et al., PTGF-β, a type 1β transforming growth factor (TGF-β) superfamily member, is a p53 target gene that inhibits tumor cell growth via TGF-β signaling pathway, Proceedings of the National Academy of Sciences, 2000, pp. 109-114, vol. 97, No. 1.

Yokoyama-Kobayashi, Midori et al., Human cDNA Encoding a Novel TGF-β Superfamily Protein Highly Expressed in Placenta, Journal of Biochemistry, 1997, pp. 622-626, vol. 122, No. 3.

Zapolski, Tomasz et al., Left atrial volume index and aortic stiffness index in adult hemodialysed patients-link between compliance and pressure mediated by endothelium dysfunction; a cross-sectional study, BMC Cardiovascular Disorders, 2012, 10 pages, vol. 12, No. 100.

Lvingston, R. J. et al., *Homo sapiens* insulin-like growth factor binding protein 7 (IGFBP7) gene, complete cds, GenBank Accession No. AY518539.1, 2004, 2 pp.

Chugh, Shaan et al., Pilot study identifying myosin heavy chain 7, desmin, insulin-like growth factor 7, and annexin A2 as circulating biomarkers of human heart failure, Proteomics, 2013, pp. 2324-2334, vol. 13.

(56) References Cited

OTHER PUBLICATIONS

Motiwala, Shweta R. et al., Measurement of Novel Biomarkers to Predict Chronic Heart Failure Outcomes and Left Ventricular Remodeling, Journal of Cardiovascular Translational Research, 2014, pp. 250-261, vol. 7.
Cappola, Thomas P. et al., Predictors of Remodeling in the CRT Era: Influence of Mitral Regurgitation, BNP, and Gender, Journal of Cardiac Failure, 2008, pp. 182-188, vol. 12, No. 3.
Brumback, Lyndia C. et al., Body size adjustments for left ventricular mass by cardiovascular magnetic resonance and their impact on left ventricular hypertrophy classification, International Journal of Cardiovascular Imaging, 2010, pp. 459-468, vol. 26, No. 4.
Cuspidi, C. et al., Prevalence of left-ventricular hypertrophy in hypertension: an updated review of echocardiographic studies, Journal of Human Hypertension, 2012, pp. 343-349, vol. 26.
Diez, Javier and Frohlich, Edward D., A Translational Approach to Hypertensive Heart Disease, Hypertension, 2010, pp. 1-8, vol. 55.
Gandhi, Parul U. et al., Prognostic Usefulness of Insulin-Like Growth Factor-Binding Protein 7 in Heart Failure With Reduced Ejection Fraction: A Novel Biomarker of Myocardial Diastolic Function?, American Journal of Cardiology, 2014, pp. 1543-1549, vol. 114.
Ginsberg, Eric et al., Soluble ST2 Predicts Incident Heart Failure and Cardiovascular Death in Older Adults, Journal of the American College of Cardiology, 2914, p. A768, vol. 63, Issue 12, 2014.
Iqbal, Navaid et al., Cardiac biomarkers: new tools for heart failure management, Cardiovascular Diagnosis and Therapy, 2012, pp. 147-164, vol. 2, No. 2.
KY, Bonnie et aL, High-Sensitivity ST2 for Prediction of Adverse Outcomes in Chronic Heart Failure, Circulation Heart =Failure, 2011, pp. 180-187, Vol. 4.
Miller, Wayne L. et al., Only Large Reductions in Concentrations of Natriuretic Peptides (BNP and NT-proBNP) are Associated with Improved Outcome in Ambulatory Patients with Chronic Heart Failure, Clinical Chemistry, 2009, pp. 78-84, vol. 55, No. 1.
Sanada, Shoji et al., IL-33 and ST2 comprise a critical biomechanically induced and cardioprotective signaling system, The Journal of Clinical Investigation, 2007, 12 pp.
Schirmer, H. et al., Prevalence of left ventricular hypertrophy in a general population the Tromso Study, European Heart Journal, 1999, pp. 429-438, vol. 20.
Schussheim, Adam E. et al., Midwall Fractional Shortening Is an Independent Predictor of Left Ventricular Diastolic Dysfunction in Asymptomatic Patients With Systemic Hypertension, American Journal of Cardiology, 1998, pp. 1056-1059, vol. 82.
Scialla, Julia J. et al., Fibroblast Growth Factor-23 and Cardiovascular Events in CKD, Journal of the American Society of Nephrology, 2014, pp. 349-360, vol. 25.
Shah, Ravi V. et al., Serum Levels of the Interleukin-1 Receptor Family Member ST2, Cardiac Structure and Function and Long-Term Mortality in Patients With Acute Dyspnea, Circulation Heart Journal, 2009, pp. 311-319, vol. 2.
Nang, Yi-Chih et al., Soluble ST2 as a Biomarker for Detecting Stable Heart Failure With a Normal Ejection Fraction in Hypertensive Patients, Journal of Cardiac Failure, 2013, pp. 163-168, vol. 19, No. 3.

\* cited by examiner

BIOMARKERS FOR RISK PREDICTION OF MORTALITY

BACKGROUND

An aim of modern medicine is to provide personalized or individualized treatment regimens. Those are treatment regimens which take into account a patient's individual needs or risks. Personalized or individual treatment regimens shall be even taken into account for measures where it is required to decide on potential treatment regimens.

Heart failure (HF) is a major and growing public health problem. It is estimated that approximately 5 million patients in the USA have HF, more than 500 000 patients are diagnosed with HF for the first time each year, and more than 250,000 patients in the US die each year of HF as a primary cause. Heart failure (HF) is one of the main causes of morbidity and mortality in developed countries. Because of aging of the population and greater longevity of patients with cardiovascular disease incidence and prevalence of HF are increasing.

Heart failure may be symptomatic or asymptomatic. It is known some subjects with asymptomatic heart failure progress more rapidly to chronic heart failure, and thus are at elevated risk of hospitalization due to heart failure and/or death (Neeland et al., Journal of the American College of Cardiology Vol. 61, No. 2, 2013). It is important to identify these subjects as early as possible since this would allow for therapeutic measures that prevent or delay the progression to chronic heart failure. The identification of rapid disease progressors and appropriate therapeutic intervention is a, however, major unmet medical need (Neeland et al.).

Neeland et al. determines of cardiac markers in patients with left ventricular hypertrophy. Based on the determination of cardiac markers, a high risk group in the general population can be identified.

WO 2014/040759 discloses that cardiac markers such as NT-proBNP and a cardiac Troponin can used for the identification of subjects who should be subjected to an imaging based diagnostic assessment.

Zapolski et al. describe the association of abnormal MFS (Midwall fractinonal shortening) and elevated levels of NTproBNP in a cross-sectional study performed in hemodialyzed patients. The investigated patients are severely ill (Zapolski et al., BMC Cardiovasc Disord. 2012, 12:100).

Satyan et al. provide data of elevated NTproBNP in combination with abnormal MFS for the identification of the mortality risk in hemodialysis patients (Satyan S, Light R P, Agarwal R Am J Kidney Dis. 2007 December; 50(6):1009-19).

Masson et al. investigate the combination of several circulating biomarkers such as NT-proBNP with abnormal midwall fractional shortening (Circulation. Nov. 25, 2014; 130: A12358 Abstract 12358: Abnormal Left Ventricular Midwall Fractional Shortening and Elevated Circulating Biomarkers Predict High Mortality in Elderly Individuals in the General Population).

BRIEF SUMMARY OF THE DISCLOSURE

The present invention relates to a method for predicting the risk of a subject of rapidly progressing to chronic heart failure and/or of hospitalization due to chronic heart failure and/or death. The method is based on the determination of at least one biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject. The method may further encompass the assessment of the presence or absence of (i) abnormal midwall fractional shortening or (ii) left ventricular hypertrophy. Further envisaged by the present invention are devices adapted to carry out the present invention.

DETAILED DESCRIPTION OF THE DISCLOSURE

Figure 1:
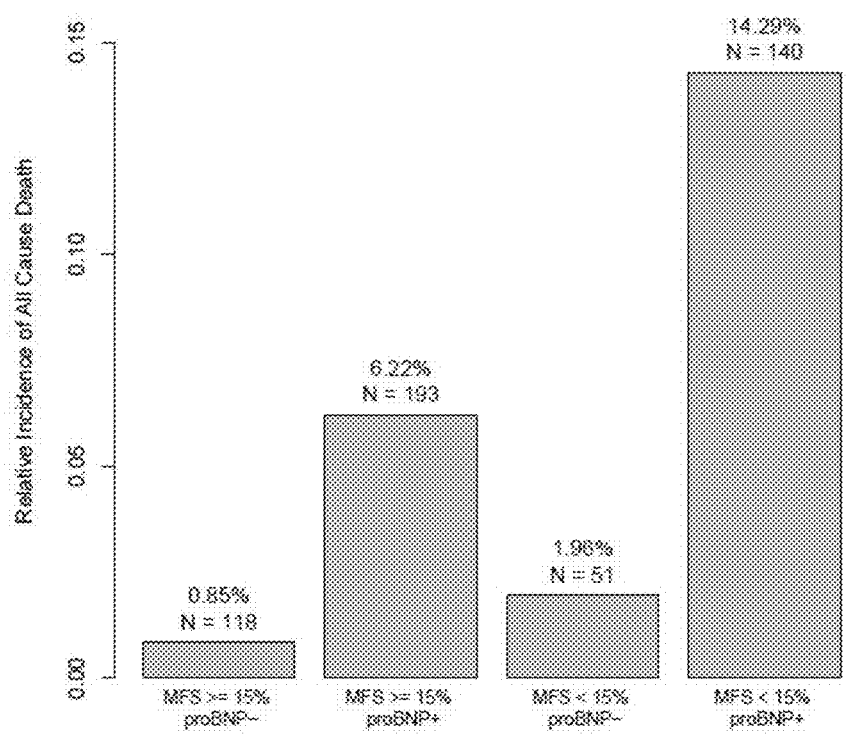
FIG. 1 Incidence for death stratified according to biomarker group (NTproBNP, MFS) in all patients.

Advantageously, it has been shown in the context of the studies underlying the present invention that the measurement of the level of at least one biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject, in combination with the assessment whether the subject suffers from abnormal MFS, or not, allows for a reliable identification of subjects who are at risk of rapidly progressing to chronic heart failure and/or who are at risk of hospitalization due to chronic heart failure and/or death. It has been further shown in the context of the studies underlying the present invention that the measurement of the level of at least one biomarker selected from the group consisting of IGFBP7 (IGF binding protein 7), soluble ST2 (sST2), FGF-23 (Fibroblast Growth Factor 23), GDF15 (Growth Differentiation Factor15) in a sample of a subject, in combination with the assessment whether the subject suffers from LVH, or not, allows for a reliable identification of subjects who are at risk of rapidly progressing to chronic heart failure and/or who are at risk of hospitalization due to chronic heart failure and/or death.

Accordingly, the present invention relates to a method for predicting the risk of a subject of rapidly progressing to chronic heart failure and/or of hospitalization due to chronic heart failure and/or death, said method comprising:

(a) assessing in said subject
  (i) the presence or the absence of abnormal midwall fractional shortening (abnormal MFS), and/or
  (ii) the presence or absence of left ventricular hypertrophy (LVH),
(b) measuring the level of at least one biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample from the subject, and
(c) comparing the level(s) of said at least one biomarker to a reference level (reference levels).

Preferably, the risk is predicted by carrying out the further step d) of predicting the risk, or of providing a prediction of the risk of the subject of rapidly progressing to chronic heart failure and/or of hospitalization due to chronic heart failure and/or of death. Said step is based on the results of steps a) b) and c).

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, the measurement steps, the calculation steps and the comparison step may in total or in part be assisted by automation, e.g., by a suitable robotic and sensory equipment for the measurement, a computer-implemented calculation algorithm on a data processing device in the calculation steps, or comparison and/or diagnosis algorithm on a data processing device in the comparison step.

In accordance with the present invention, the risk of a subject of rapidly progressing to chronic heart failure and/or of hospitalization due to chronic heart failure and/or of death shall be predicted. Thus, a subject can be identified who is at risk thereof, or who is not at risk thereof. The term "predicting the risk" as used herein, preferably, refers to assessing the probability according to which a subject will rapidly progress to chronic heart failure and/or to assessing the probability of hospitalization due to chronic heart failure and/or of death. More preferably, the risk/probability within a certain time window is predicted. In a preferred embodiment of the present invention, the predictive window, preferably, is an interval of at least 1 year, at least 2 years, at least 3 years, at least 4 years, at least 5 years, or at least 10 years, or any intermitting time range. In a particular preferred embodiment of the present invention, the predictive window, preferably, is an interval of 5 years, more preferably of 4 years, or most preferably, of 3 years. In another preferred embodiment of the present invention, the predictive window will be the entire life span of the subject. Preferably, said predictive window is calculated from the time point at which the sample to be tested has been obtained.

As will be understood by those skilled in the art, such a prediction is usually not intended to be correct for 100% of the subjects. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001. Preferably, the probability envisaged by the present invention allows that the prediction of an increased, normal or decreased risk will be correct for at least 60%, at least 70%, at least 80%, or at least 90% of the subjects of a given cohort or population. The term, preferably, relates to predicting whether a subject is at elevated risk or reduced risk as compared to the average risk in a population of subjects.

The term "predicting the risk" as used herein means that the subject to be analyzed by the method of the present invention is allocated either into the group of subjects being at risk of rapidly progressing to chronic heart failure and/or of hospitalization due to chronic heart failure and/or death, or into the group of subjects being not at risk of rapidly progressing to chronic heart failure and/or of hospitalization due to chronic heart failure and/or death. At subject who is at risk, preferably, is a subject who is at elevated risk of rapidly progressing to chronic heart failure and/or of hospitalization due to chronic heart failure and/or death (in particular within the predictive window). Preferably, said risk is elevated as compared to the average risk in a cohort of subjects (i.e. a group of subjects). At subject who is not at risk, preferably, is a subject who is at reduced risk of rapidly progressing to chronic heart failure and/or of hospitalization due to chronic heart failure and/or death (in particular within the predictive window). Preferably, said risk is reduced as compared to the average risk in a cohort of subjects (i.e. a group of subjects). Accordingly, the method of the present invention allows for differentiating between an elevated risk or a reduced risk. A subject who is at risk of preferably has a risk of 12% or larger, or, more preferably of 15% or larger, or most preferably of 20% or larger of rapidly progressing to chronic heart failure and/or of hospitalization due to chronic heart failure and/or death, preferably, within a predictive window of 3 or 4 years. A subject who is not at risk preferably has a risk of lower than 10%, more preferably of lower than, 8%, or most preferably of lower than 7% of rapidly progressing to chronic heart failure and/or of hospitalization due to chronic heart failure and/or death, preferably, within a predictive window of 3 or 4 years.

In an embodiment, the risk of hospitalization is predicted. The expression "hospitalization" as used herein, preferably, means that the subject is admitted to a hospital, in particular on an in-patient basis. The hospitalization should be due to chronic heart failure. Thus, chronic heart failure shall be the cause for the hospitalization. In an embodiment, the risk of the subject of rapidly progressing to chronic heart failure is predicted. The expression "rapidly progressing to chronic heart failure" is well understood by the skilled person. A subject who progresses rapidly to chronic heart failure, preferably, is a subject who progresses to chronic heart failure within a window period as described elsewhere herein. Chronic heart failure preferably means heart failure classified as stage C or D according to according to the ACC/AHA classification (for the ACC/AHA classification, see elsewhere herein). If the subject to be tested has heart failure classified as stage A according to according to the ACC/AHA classification (or if the subject does not suffer from heart failure), the term "chronic heart failure" may mean heart failure classified as stage B, C or D.

In an embodiment, the risk of death is predicted. The term "death" as used herein preferably relates to death from any cause, and, more preferably, to death from cardiac cause, and most preferably to death due to heart failure.

The phrase "providing a prediction" as used herein refers to using the information or data generated relating to the level a biomarker as referred to herein in a sample of a subject, and relating to the presence of absence of (i) abnormal MFS or (ii) LVH to predict a risk as referred to herein. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of the biomarker(s) to a reference level (or levels). In some embodiments, the information or data includes an indication that the subject is diagnosed to be at risk.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a human subject. Preferably, the subject is 65 years or older, more preferably, the subject is 75 years old or older, most preferably, the subject is 80 years old or older. The terms "subject" and "patient" are used interchangeably herein.

In a preferred embodiment of the present invention, the subject is apparently healthy with respect to heart failure. A subject who is apparently healthy with respect to heart failure preferably does not show symptoms of heart failure (and thus is asymptomatic with respect to heart failure). A subject who does not show symptoms of heart failure preferably has no limitation of physical activity, and ordinary physical activity results in undue breathlessness, fatigue, or palpitations. However, it is envisaged that subject has heart failure classified as stage A or B according to the ACC/AHA classification, in particular heart failure classified as stage A, or early stage B according to the ACC/AHA classification.

The ACC/AHA classification is a classification for heart failure developed by the American College of Cardiology and the American Heart Association (for the classification, see J. Am. Coll. Cardiol. 2001; 38; 2101-2113, updated in 2005, see J. Am. Coll. Cardiol. 2005; 46; e1-e82 which is herewith incorporated by reference in its entirety). The classification is also described in Mureddu et al., European Journal of Heart Failure (2012) 14, 718-729 which is herewith incorporated by reference as well. 4 stages A, B, C and D are defined. Stages A and B are not HF (heart failure) but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate impaired LV function would be designated as stage B. Stage C then denotes patients with current or past symptoms of HF associated with underlying structural heart disease (the bulk of patients with HF), and stage D designates patients with truly refractory HF. The ACC/AHA classification and the term "heart failure" are also explained in WO 2012/025355 which herewith is incorporated by reference in its entirety.

Preferably, the subject in the context of the present invention does not have impaired renal function. Preferably, the subject shall not suffer from renal failure, in particular the subject shall not suffer from acute, chronic and/or end stage renal failure. Thus, the subject preferably is preferably not a hemodialyzed subject.

How to assess whether a subject exhibits impaired renal function is well known in the art. Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. All calculations derived from formulas such as the Cockgroft Gault formula of the MDRD formula deliver estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min). The normal range of GFR for males is 97 to 137 mL/min, the normal range of GFR for females is 88 to 128 ml/min. Thus, it is particularly contemplated that the GFR of a subject who does not exhibit impaired renal function is within this range. Moreover, said subject preferably, has a blood creatinine level (in particular a serum creatinine level) of lower than 0.9 mg/dl, more preferably of lower than 1.1 mg/dl and most preferably of lower than 1.3 mg/dl.

Step (a) of the aforementioned method of the present invention comprises two alternative embodiments: (i) and (ii). According to alternative (i), the presence or the absence of abnormal midwall fractional shortening (abnormal MFS) is assessed. According to alternative (ii), the presence or absence of left ventricular hypertrophy (LVH) is assessed.

It has been shown in the context of the methods of the present invention, that the risk of the subject can be predicted even before the subject suffers from left ventricular hypertrophy (embodiment (i)). However, the risk can be also reliably predicted, if the subject suffers from LVH (embodiment (ii)).

If embodiment (i) of step (a) of the aforementioned method is carried out, the subject preferably does not suffer from LVH. The term "left ventricular hypertrophy" is well known in the art. A detailed overview on left ventricular hypertrophy can be, e.g. found in standard text books (see Swamy Curr Cardiol Rep (2010) 12:277-282). LVH can be detected by electrocardiography, echocardiography, or cardiac magnetic resonance imaging (MRI). Preferably, LVH is detected by echocardiography. Moreover, criteria for the diagnosis of LVH are well known in the art (Mancia et al., European Heart J. 2007, 28: 1462, Die Innere Medizin:

Referenzwerk für den Facharzt—Wolfgang Gerok—2007, page 293, Swamy Curr Cardiol Rep (2010) 12:277-282). The term "left ventricular hypertrophy" (abbreviated "LVH") as used herein, preferably, relates to a thickening of the walls of the ventricles. LVH is, preferably, a response to a chronically increased workload on the heart. LVH is found in patients suffering from arterial hypertension is a disease requiring treatment. In the context of the present invention the risk is predicted before the subject suffers from LVH. Accordingly, the subject to be tested preferably does not suffer from LVH. A subject who does not suffer from LVH, preferably, has a normal left ventricular mass.

However, it is also envisaged that the subject may suffer from LVH, if embodiment (i) of step (a) of the aforementioned method is carried out.

The diagnosis of LVH and thus the assessment of the left ventricular mass, preferably, includes measurements of the septum diameter, left ventricular posterial wall thickness and end diastolic diameter, with calculation of left ventricular mass according to formulae known in the art. Particularly preferred criteria for diagnosing LVH are e.g. disclosed in the guidelines (Mancia et al., European Heart J. 2007, 28: 1462). Preferably, the Cornell voltage criteria, the Cornell product criteria, the Sokolow-Lyon voltage criteria or the Romhilt-Estes point score system is/are used for the diagnosis of LVH and thus for the assessment of the left ventricular mass (see e.g. Mancia et al., European Heart J. 2007, 28: 1462).

If the subject is male, the following applies: a subject is considered to have a normal left ventricular mass (and thus does not suffer from LVH), if the left ventricular mass index of the male subject is, preferably, equal to or lower than 105 $g/m^2$, or, more preferably, is equal to or lower than 110 $g/m^2$, or, most preferably, is equal to or lower than 115 $g/m^2$. If the subject is female, the following applies: a subject is considered to have a normal left ventricular mass, if the left ventricular mass index of the subject is, preferably, equal to or lower than 85 $g/m^2$, or, more preferably, is equal to or lower than 90 $g/m^2$, or, most preferably, is equal to or lower than 96 $g/m^2$. It is to be understood that a subject who has a normal left ventricular mass does not suffer from LVH (see, e.g. Drazner M H, Dries D L, Peshock R M, Cooper R S, Klassen C, Kazi F, Willett D, Victor R G. Left ventricular hypertrophy is more prevalent in blacks than whites in the general population: the Dallas Heart Study. Hypertension. 2005; 46:124-129).

In step (a), embodiment (i), of the method of the present invention, the presence or the absence of abnormal midwall fractional shortening (abnormal MFS) shall be assessed. Thus, it is assessed whether the subject suffers from abnormal MFS, or not. A subject who does not suffer from abnormal MFS has a normal MFS.

The expression "midwall fractional shortening" is well known in art (abbreviated herein as "MFS"). MFS is an early sign of LV dysfunction is reduced LV midwall fractional shortening. Preferably, midwall fractional shortening is considered as abnormal, if it is lower than 15%. This cut-off point has been used as a reference value in the setting of HF and has demonstrated prognostic relevance in hypertensive subjects (see Murredu et al., European Journal of Heart Failure (2012) 14, 718-729). Also preferably, midwall fractional shortening is considered as abnormal, if it is lower than 14%, or 13%. Further, midwall fractional shortening is considered as normal, if it is larger than (or equal to) 15%. Also preferably, midwall fractional shortening is considered as normal, if it is larger than 16%, or 17%.

How to determine midwall fractional shortening (or LVH) and thus how to assess the presence or the absence of abnormal midwall fractional shortening (or LVH) in a subject is well known in the art. Preferably, the assessment is based on echocardiographic images of the heart obtained from the subject to be tested. The images shall allow for assessing the presence or absence of abnormal midwall fractional shortening (or LVH). They may be obtained by any echocardiography technique deemed appropriate, in particular M-mode echocardiography, 2D speckle tracking echocardiography, Doppler echocardiography, or two-dimensional (2D) echocardiography.

In an embodiment, midwall fractional shortening may be calculated from the two-shell cylindrical model as described by Shimizu et al. which is herewith incorporated by reference with respect to its entire disclosure content (Shimizu G, Hirota Y, Kita Y, Kawamura K, Saito T, Gaasch W H. Left ventricular midwall mechanics in systemic arterial hypertension. Circulation 1991; 83:1676-84)). This method is a refinement of the conventional midwall method and provides data that reflect shortening of a theoretic circumferential midwall fiber or ring of myocardium. It assumes a constant left ventricular mass throughout the cardiac cycle and does not require the assumption that inner and outer wall thickening fractions are equal. The determination of MFS is also described by Mayet et al. or in earlier papers from Shimizu et al. all of which are herewith incorporated by reference. (see e.g. Mayet et al., Hypertension. 2000; 36: 755-759; Shimizu G, Zile M R, Blaustein A S, Gaasch W H. Left ventricular chamber filling and midwall fiber lengthening in patients with left ventricular hypertrophy: overestimation of fiber velocities by conventional midwall measurements. Circulation. 1985; 71:266-272, or Shimizu G, Conrad C H, Gaasch W H. Phase-plane analysis of left ventricular chamber filling and midwall fiber lengthening in patients with left ventricular hypertrophy. Circulation. 1987; 75(suppl I):I-34-I-39). Moreover, the determination of MFS has been described by de Simone et al. (JACC, 1994, Vol. 23(6): 1444-51) which is also incorporated by reference in its entirety. In another embodiment, MFS is assessed as described by Mureddu et al. (European Journal of Heart Failure (2012) 14, 718-729). Preferably, MFS as used herein is determined according to the method as described by Shimizu in 1987 or 1985, more preferably MFS, is determined according to Mayet et al., even more preferably, MFS is determined according to de Simone, and most preferably, MFS is determined as described by Mureddu.

As further described in the Examples section, the measurement of the level of at least one biomarker as referred to herein is in particular advantageous in subjects who suffer from abnormal MFS (see also Figures). In subjects with abnormal MFS, the measurement of the at least one biomarker allows for a very reliable differentiation between a subject who is at risk and who is not risk. The results in the Examples section show that a subject might be have a very low risk, although he suffers from abnormal midwall fractional shortening. However, there are also subjects who suffer from abnormal MFS and who have a very high risk. The determination of at least one biomarker as referred to herein allows to identify those subjects who have a high risk and a low risk.

The discriminatory power of some biomarkers as referred to herein (in particular of a BNP-type peptide, in particular NT-proBNP, sST2, IGFBP7, a cardiac Troponin, in particular cTnT, and/or FGF23 is particularly advantageous in subjects who have a normal ventricular mass but an abnormal MFS. Thus, if embodiment (i) of step (a) is carried out, the at least one biomarker is preferably, a BNP-type peptide, sST2, IGFBP7, a cardiac Troponin and/or FGF23. Preferably, the marker is sST2, more preferably, the marker is IGFBP7, most preferably, the marker is NT-proBNP. In addition also preferred that the marker is Troponin T or FGF23. It is to be understood that the biomarker GDF-15 and/or may be determined as well.

In an embodiment, step b) may be carried out after the presence or absence of abnormal MFS has been assessed. In particular, step b) may carried out in a subject who suffers from abnormal MFS. Accordingly, the method of the present in invention may further comprises step a1) of selecting a subject who suffers from abnormal midwall fractional shortening based on the assessment in step a). Thus, the level of the at least biomarker is measured in a subject suffering from abnormal MFS.

Alternatively, the level of the at least one biomarker may be measured as a first step. Afterwards, the presence of abnormal midwall fractional shortening is assessed.

In step (a), embodiment (ii), of the method of the present invention, the presence or the absence of LVH shall be assessed. Thus, it is assessed whether the subject suffers from LVH, or not. A subject who does not suffer from LVH has a normal left ventricular mass (as outlined elsewhere herein.

If embodiment (ii) of step (a) of the aforementioned method is carried out, the at least one biomarker is preferably selected from IGFBP7 (IGF binding protein 7), soluble ST2 (sST2), FGF-23 (Fibroblast Growth Factor 23), and GDF15 (Growth Differentiation Factor15). In particular, the at least one biomarker is IGFBP-7 and/or sST2. However, the remaining markers such as NT-proBNP may be determined as well. Preferred combinations of biomarkers (patient's characteristics) are as follows:

IGFBP7+a BNP-type peptide, in particular NTproBNP
ST2+a BNP-type peptide, in particular NTproBNP
FGF23+a BNP-type peptide, in particular NTproBNP
IGFBP7+ST2
age+a BNP-type peptide, in particular NTproBNP
age+NTproBNP+cTn, in particular hs-cTnT "Age" preferably means that the subject to be tested is 65 years or older Another preferred combination is a BNP-type peptide, in particular NTproBNP, and IGFBP7, in particular in aged subjects (in particular a subject is 65 years or older), preferably in combination with the assessment of the presence or absence of left ventricular hypertrophy (LVH).

Another preferred combination is a BNP-type peptide, in particular NTproBNP, and IGFBP7, in particular in aged subjects (in particular a subject is 65 years or older) in combination with the assessment of the presence or absence of abnormal MFS.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. In particular, it is envisaged that the sample is a blood, blood serum, or blood plasma sample.

In accordance with the present invention, the level of at least one biomarker as referred to herein shall be measured. The term "at least one" means one or more than one. Preferably, the level(s) of one, two, three, four, five, six, seven, or eight biomarkers are measured in the context of the present invention.

Moreover, it is envisaged that the level of at least one further biomarker is measured level and that the measured level of the at least one further biomarker is compared to a reference level. Preferably, the at least one further biomarker is PlGF (Placental Growth Factor). More preferably, the at least one further biomarker is MMP2 (matrix metalloproteinase-2). MMP2 (also known as 72 kDa type IV collagenase and gelatinase A) is an enzyme that in humans is encoded by the MMP2 gene (for the sequence of human MMP2, see e.g. Uniprot (P08253).

In addition, it is envisaged to assess a further characteristic or further characteristics of the subject for the assessment of the risk, preferably age or gender (sex), in particular age and gender (sex). Preferably, the risk is predicted based on the comparison step and based on the patient's characteristic(s) (such as age and sex). More preferably, the risk is predicted based on the comparison step, based on the presence or absence of abnormal MFS and/or LVH (in particular, based on the presence of MFS and/or LVH), and based on the patient's characteristic(s) (such as age and sex).

Figure 11:
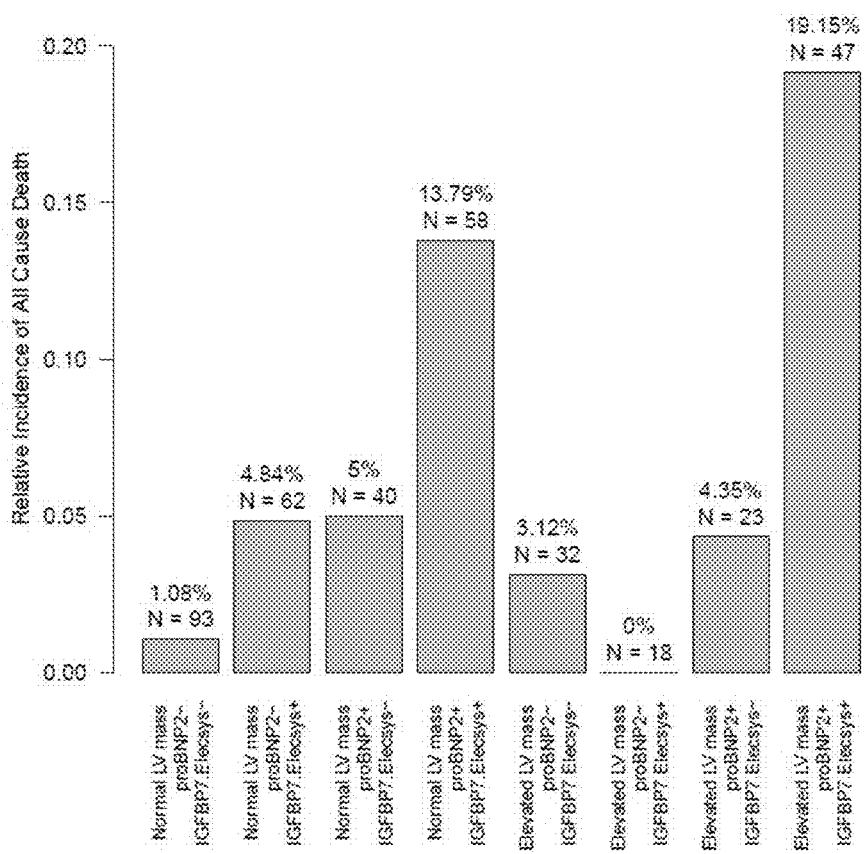
FIG. 11 Incidence for death stratified according to biomarker group (NTproBNP, IGFBP7, LVH) in all patients.
Figure 12:
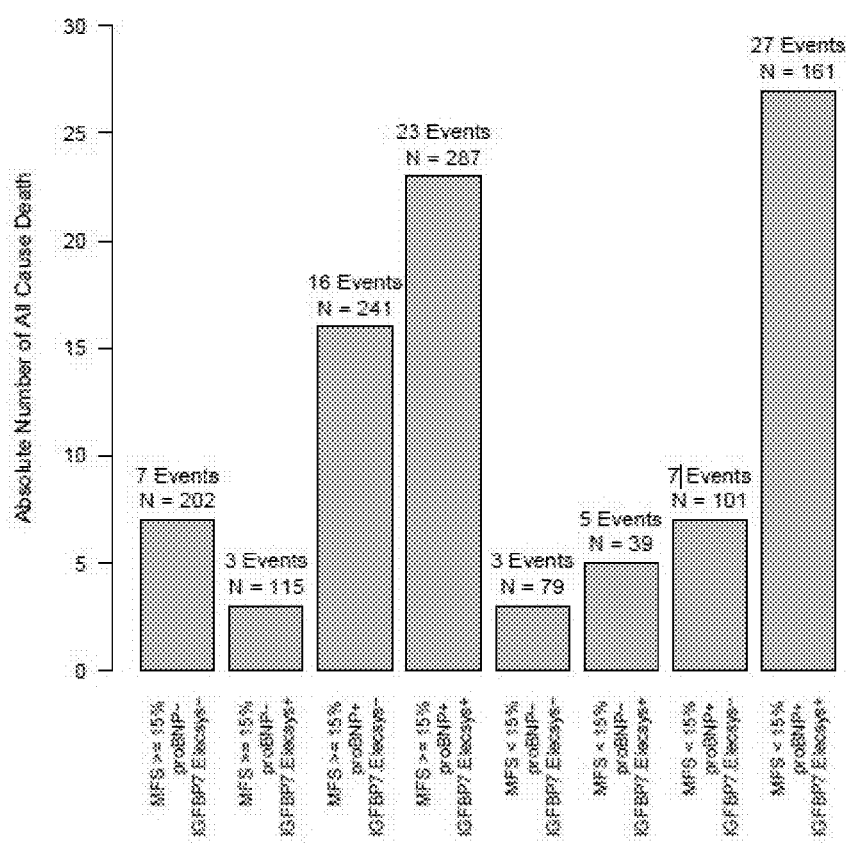
FIG. 12 Incidence for death stratified according to biomarker group (NTproBNP, IGFBP7, MFS) in all patients.

In a preferred embodiment, the levels of biomarkers are measured in combination. Thus, more than one level is measured. Moreover, combinations of a biomarker (or of biomarkers) with a patient's characteristic (patient's characteristics) are envisaged. Preferred combinations are shown in FIG. 11 and FIG. 12 and, in particular in Table 1 of the Examples section, in particular, the combination of a BNP-type peptide, in particular NTproBNP and IGFBP7 with the assessment of LVH or MFS, respectively, is preferred. Further preferred combinations are shown in Table 2 of the Examples section.

Further preferred combinations of biomarkers (and patient's characteristics) are:
  a BNP-type peptide, in particular NTproBNP, and a cardiac Troponin, in particular cTnT
  IGFBP7 and a BNP-type peptide, in particular NT-proBNP
  IGFBP7 and ST2
  ST2 and a BNP-type peptide, in particular NT-proBNP
  GDF15 and a BNP-type peptide, in particular NT-proBNP
  FGF23 and a BNP-type peptide, in particular NT-proBNP
  Age and a BNP-type peptide, in particular NT-proBNP
  Age, a cardiac Troponin, in particular cTnT (Troponin T) and a BNP-type peptide, in particular NT-proBNP Further preferred combinations are: at least one biomarker selected from biomarker selected from a cardiac Troponin, in particular TnT, FGF23, a BNP-type peptide, in particular NTproBNP, IGFBP7, sST2, and GDF15, in combination with age and/or (in particular and) gender.

The term "measuring" (herein also referred to a "determining") the level of a marker as referred to herein refers to the quantification of the biomarker, e.g. to determining the level of the biomarker in the sample, employing appropriate methods.

The biomarkers to be measured in connection with the present invention are protein biomarkers. How to measure the level, and thus how to determine the amount of a protein biomarker is well know in the art and is e.g. described in WO 2014/040759 which is herewith incorporated by reference in its entirety, see in particular page 15, line 15, to page 19 line 25.

In an embodiment, the level of the at least one biomarker is measured by contacting the sample with a binding agent that specifically binds to the respective marker, thereby forming a complex between the agent and said marker, detecting the level of complex formed, and thereby measuring the level of said marker.

Preferably, the binding agent binds specifically to a biomarker as referred to herein. Preferred binding agents include antibodies, nucleic acids, peptides or polypeptides such as receptors or binding partners for the peptide or polypeptide and fragments thereof comprising the binding domains for the peptides, and aptamers, e.g. nucleic acid or peptide aptamers, in particular antibodies. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule. Preferably, the level of binding to a molecule other than the target molecule results in a binding affinity which is only 10% or less, more preferably only 5% or less of the affinity to the target molecule.

Third, the binding agent may be coupled covalently or non-covalently to a label allowing detection and measurement of the binding agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent.

The biomarkers as referred to herein are well known in the art.

The Brain Natriuretic Peptid type peptide (herein also referred to as BNP-type peptide) is preferably selected from the group consisting of pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, brain natriuretic peptides according to the present invention are NT-proBNP, BNP, and variants thereof. BNP is the active hormone and has a shorter half-life than its respective inactive counterpart NT-proBNP. Preferably, the Brain Natriuretic Peptid-type peptide is BNP (Brain natriuretic peptide), and more preferably NT-proBNP (N-terminal of the prohormone brain natriuretic peptide).

The term "cardiac Troponin" refers to all Troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac Troponin refers to Troponin T and/or Troponin I, and, most preferably, to Troponin T.

IGF binding protein 7 (=IGFBP7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). Preferably, the term "IGFBP7" refers to human IGFBP7. The sequence of the protein is well known in the art and is e.g. accessible via GenBank (NP_001240764.1).

ST2, also known as "Interleukin 1 receptor-like 1" is a member of the IL-1 receptor family that is produced by cardiac fibroblasts and cardiomyocytes under conditions of mechanical stress. ST2 is an interleukin-1 receptor family member and exists in both membrane-bound isoform and a soluble isoform (sST2). In the context of the present invention, the amount of soluble ST2 shall be determined (see Dieplinger et al. (Clinical Biochemistry, 43, 2010: 1169 to 1170). ST2 also known as Interleukin 1 receptor-like 1 or IL1RL1, is encoded in humans by the IL1RL1 gene. The sequence of the human ST2 polypeptide is well known in the art, and e.g. accessible via GenBank, see NP_003847.2 GI:27894328.

The biomarker fibroblast growth factor-23 (abbreviated "FGF-23") is well known in the art. FGF-23 a key player in the regulation of calcium-phosphate and vitamin D metabolism and has a causal role in the pathogenesis of LV hypertrophy, a major determinant of cardiovascular events. Preferably, FGF-23 is human FGF-23. The sequence of human FGF-23 is well known in the art, e.g. the amino sequence can be assessed via GenBank accession number NM_020638.1 GI:10190673. Moreover, the sequence is also disclosed in Shimada et al., 2001, PNAS, vol. 98(11) page 6500 to 6505.

The term "Growth-Differentiation Factor-15" or "GDF-15" relates to a polypeptide being a member of the transforming growth factor (TGF) cytokine superfamily. The terms polypeptide, peptide and protein are used interchangeable throughout this specification. GDF-15 was originally cloned as macrophage-inhibitory cytokine 1 and later also identified as placental transforming growth factor-15, placental bone morphogenetic protein, non-steroidal anti-inflammatory drug-activated gene 1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441.

Intercellular adhesion molecule-1 (ICAM-1; frequently also referred to as CD54) is a transmembrane glycoprotein which is typically expressed on endothelial cells and cells of the immune system. The structure of ICAM-1 is characterized by heavy glycosylation and consists of an extracellular portion, which forms five immunoglobulin (Ig)-like domains. These domains are attached to a single transmembrane region and a short cytoplasmic tail. Several ligands for ICAM-1 have been described; it binds to integrins of type CD11a/CD18, or CD11b/CD18 and is also exploited by Rhinovirus as a receptor. The amino acid sequence of human ICAM-1, preferably, is given in UniProt Entry P05362. The ICAM-1 referred to in accordance with the present invention further encompasses allelic and other variants of said specific sequence.

The marker "Angiopoietin 2" (ANG2) is well known in the art (see e.g. Sarah Y. Yuan; Robert R. Rigor (30 Sep. 2010). Regulation of Endothelial Barrier Function. Morgan & Claypool Publishers. ISBN 978-1-61504-120-6). Angiopoietin 2 is part of a family of vascular growth factors that play a role in embryonic and postnatal angiogenesis. Angiopoietin-2 is produced and stored in Weibel-Palade bodies in endothelial cells and acts as a TEK tyrosine kinase antagonist. angiopoietin-2 is a marker for early cardiovascular disease in children on chronic dialysis (Shroff et al. (2013). "Circulating angiopoietin-2 is a marker for early cardiovascular disease in children on chronic dialysis.". PLoS ONE 8 (2): e56273). The sequence of ANG2 is e.g. accessible via UniProt (see Accession Number O15123)

The term "level" as used herein encompasses the absolute amount of a biomarker as referred to herein, the relative amount or concentration of the said biomarker as well as any value or parameter which correlates thereto or can be derived therefrom.

The term "comparing" as used herein refers to comparing the level of the biomarker in the sample from the individual or patient with the reference level of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. The value of the measured or detected level of the biomarker in the sample from the individual or patient and the reference level can be, e.g., compared to each other and the said comparison can be automatically carried out by a computer program executing an algorithm for the comparison.

The term "reference level" is well known in the art. Preferred reference levels can be determined by the skilled person without further ado. Preferably, the term "reference level" herein refers to a predetermined value for the respective biomarker. In this context "level" encompasses the absolute amount, the relative amount or concentration as well as any value or parameter which correlates thereto or can be derived therefrom. Preferably, the reference level is a level which allows for allocating the subject into a group of subjects who are at risk of rapidly progressing to chronic heart failure and/or of hospitalization due to chronic heart failure and/or death, or into a group of subjects who are not at risk of rapidly progressing to chronic heart failure and/or of hospitalization due to chronic heart failure and/or death. Thus, the reference level shall allow for differentiating between a subject who is at risk or who is not at risk (of rapidly progressing to chronic heart failure and/or of hospitalization due to chronic heart failure) and/or death.

As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. In one embodiment the reference level is determined in a reference sample or samples from a patient (or group of patients) who are at risk. In another embodiment, the referenced is determined in a reference sample or samples from a patient (or group of patients) who are not at risk (of rapidly progressing to chronic heart failure and/or of hospitalization due to chronic heart failure and/or death). The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated. In one embodiment the reference level is set to the median value as determined from the overall distribution of the values in a disease entity investigated. The reference level may vary depending on various physiological parameters such as age, gender or subpopulation, as well as on the means used for the determination of the biomarkers referred to herein. In one embodiment, the reference sample is from essentially the same type of cells, tissue, organ or body fluid source as the sample from the individual or patient subjected to the method of the invention, e.g. if according to the invention blood is used as a sample to determine the level of biomarkers in the individual, the reference level is also determined in blood or a part thereof.

Preferably, the following applies as algorithm:

Preferably, a level (or levels) of the at least one biomarker above the reference level(s) in indicates that the subject is at risk of rapidly progressing to chronic heart failure and/or of hospitalization due to chronic heart failure and/or death. Also preferably, a level (or levels) of the at least one biomarker below the reference level(s) indicates that the subject is not at risk of rapidly progressing to chronic heart failure and/or of hospitalization due to chronic heart failure and/or death.

The aforementioned algorithm applies in particular, if the presence of abnormal MFS or LVH has been assessed in step a) of the method of the present invention, i.e. if it has been assessed in step a) that the subject suffers from abnormal MFS or from LVH.

In certain embodiments, the term "larger than the reference level" or "above the reference level" refers to a level of the biomarker in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in biomarker level in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample. In certain embodiments, the term "lower than the reference level" or "below" herein refers to a level of the biomarker in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease in biomarker level in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

Preferred reference levels can be determined by the skilled person without further ado. The reference level may be age-dependent. However, this is taken into account by the skilled person. For example, the reference level may be the median level in a population of subjects. Preferred reference levels for the markers disclosed herein are shown in the Examples section in Table 3. Depending on the desired sensitivity and specificity, the reference levels may differ.

In a preferred embodiment of the methods of the present invention, said methods further comprise the step of recommending and/or initiating at least one suitable therapy, if it is predicted that the subject is at risk of rapidly progressing to chronic heart failure and/or of hospitalization due to chronic heart failure and/or death. Accordingly, the present invention also pertains the a method of treatment.

Preferably, a The term "therapy" as used in the context of the present invention encompasses life style changes, diet regimen, interventions on the body as well as medicinal treatment, i.e. treatment with a medicament (or with medicaments).

Medicaments suitable for the treatment are well known in the art, see e.g. Heart Disease, 2008, 8th Edition, Eds. Braunwald, Elsevier Sounders, chapter 24 (in respect to heart failure) and chapter 41 (in respect to hypertension). These treatments are a part of the present invention. Preferably, the administration of such medicaments aims to reduce the risk of the subject rapidly progressing to chronic heart failure and/or of hospitalization due to chronic heart failure and/or death. Preferably, the medicament is selected from the group consisting of an angiotensin-converting enzyme (ACE) inhibitors, an angiotensin receptor antagonist (ARB), an aldosterone antagonists, a diuretic and a beta blocker. In particular, the medicament is an angiotensin receptor antagonist, or an ACE inhibitor.

Preferred diuretics are loop diuretics, thiazide and thiazide-like diuretics. Preferred beta blockers are proprenolol, metoprolol, bisoprolol, carvedilol, bucindolol, and nebivolol. Preferred ACE inhibitors are Enalapril, Captopril, Ramipril and Trandolapril. Preferred angiotensin receptor antagonists are Losartan, Valsartan, Irbesartan, Candesartan, Telmisartan, and Eprosartan. Preferred aldosterone antagonists like Eplerone, Spironolactone, Canrenone, Mexrenone and Prorenone. Preferred calcium antagonists are dihydropyridines, verapamil, and diltiazem.

Life style changes include smoking cessation, moderation of alcohol consumption, increased physical activity, weight loss, sodium (salt) restriction, weight management and healthy eating, daily fish oil, salt restriction.

Further preferred therapies are disclosed by Frohlich et al. (Journal of Hypertension 2011, 29:17-26), which is herewith incorporated by reference with respect to its entire disclosure content. In particular, it is referred to page 21 and 22 of this reference.

The definitions given herein below apply mutatis mutandis to the following embodiments of the present invention.

The present invention also relates to the use of at least one biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject, in combination with a) echocardiographic images of the heart obtained from said subject, wherein said images allow for assessing the presence or absence of (i) abnormal MFS, and/or (ii) LVH in said subject, or b) an echocardiography device which preferably allows for assessing the presence or absence of (i) abnormal MFS, and/or (ii) LVH in said subject, for predicting the risk of the subject of rapidly progressing to chronic heart failure and/or of hospitalization due to chronic heart failure and/or death.

The present invention also relates to the use of at least one binding agent which binds to a biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject, in combination with a) echocardiographic images of the heart obtained from said subject, wherein said images allow for assessing the presence or absence of abnormal (i) abnormal MFS, and/or (ii) LVH in said subject, or b) an echocardiography device which preferably allows for assessing the presence or absence of (i) abnormal MFS, and/or (ii) LVH in said subject, for predicting the risk of the subject of rapidly progressing to chronic heart failure and/or of hospitalization due to chronic heart failure and/or death.

Preferably, the echocardiography device as referred to herein is used for the assessment of the presence or absence of (i) abnormal MFS, and/or (ii) LVH.

The term "binding agent" has been defined above. Preferably, the binding agent binds specifically to a biomarker as referred to herein. More preferably, the binding agent is an antibody or a fragment thereof. At least one binding agent may be used. If the level of more than one biomarker shall be determined, more than one binding agent is used. E.g. if the levels of a BNP-type peptide and IGFBP7 shall be measured, a binding agent which binds to the BNP-type peptide and an binding agent which binds to IGFBP7 is used.

Furthermore, a device adapted for carrying out the method of the present invention is provided, said device comprising a) an analyzer unit comprising at least one binding agent for measuring the level of at least one marker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject, b) a data input means for inputting the information whether the subject suffers from (i) abnormal MFS, and/or (ii) LVH, and c) an evaluation unit for comparing the measured level(s) with reference level(s), whereby based on the results of comparing the measured level(s) with the reference level(s), and based on the information whether the subject suffers from (i) abnormal MFS, and/or (ii) LVH, the risk of the subject of rapidly progressing to chronic heart failure and/or of hospitalization due to chronic heart failure and/or death is predicted, said unit comprising a database with a reference level (or levels) and a computer-implemented algorithm carrying out the comparison.

The term "device" as used herein relates to a system comprising the aforementioned units operatively linked to each other as to allow the diagnosis according to the methods of the invention. Preferred binding agents which can be used for the analyzer unit are disclosed elsewhere herein. The analyzer unit, preferably, comprises said agents in immobilized form on a solid support which is to be contacted to the sample comprising the biomarkers the level of which is to be measured. Moreover, the analyzer unit can also comprise a detector which measures the level of detection agent which is specifically bound to the biomarker(s). The measured level(s) can be transmitted to the evaluation unit.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path.

Said evaluation unit preferably, comprises a data processing element, such as a computer or computing device. Preferably, said element has an implemented algorithm for carrying out a comparison of said level(s) to a reference level (or reference level), wherein based on the results of the comparison and based an the information whether the subject suffers from abnormal midwall fractional shortening, the risk of a subject of rapidly progressing to chronic heart failure and/or of hospitalization due to chronic heart failure and/or death is predicted. The results may be given as output of parametric diagnostic raw data. It is to be understood that these data will usually need interpretation by the clinician. However, also envisaged are expert system devices wherein the output comprises processed diagnostic raw data the interpretation of which does not require a specialized clinician.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. A computing device has access to a memory. A memory is a computer readable medium and may comprise a single storage device or multiple storage devices, located either locally with the computing device or accessible to the computing device across a network, for example. The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself.

The definitions given herein below apply mutatis mutandis to the following embodiments of the present invention.

In addition, the present invention relates to a method for predicting the risk of a subject of rapidly progressing to chronic heart failure and/or of hospitalization due to chronic heart failure and/or death, said method comprising:

(a) measuring the level of at least one biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample from a subject who suffers from (i) abnormal MFS, and/or (ii) LVH, and (b) comparing the level of said at least one biomarker to a reference level.

Preferably, the risk is predicted by carrying out the further step c) of predicting the risk of the subject of rapidly progressing to chronic heart failure and/or of hospitalization due to chronic heart failure and/or of death. Said step is based on the results of step b).

The subject who suffers from abnormal MFS (alternative (i)) may or may not suffer from LVH. In particular, it is envisaged that the subject does not suffer from LVH.

Preferred biomarkers and biomarker combinations for alternatives (i) and (ii) are disclosed elsewhere herein. Moreover, the reference level as well as preferred diagnostic algorithms are described elsewhere herein. Preferably, a level (or levels) of the at least one biomarker above the reference level(s) in indicates that the subject is at risk of rapidly progressing to chronic heart failure and/or of hospitalization due to chronic heart failure and/or death. Also preferably, a level (or levels) of the at least one biomarker below the reference level(s) indicates that the subject is not at risk of rapidly progressing to chronic heart failure and/or of hospitalization due to chronic heart failure and/or death.

The present invention also relates to the use at least one biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject who suffers from (i) abnormal MFS, and/or (ii) LVH for predicting the risk of the subject of rapidly progressing to chronic heart failure and/or of hospitalization due to chronic heart failure and/or death.

The present invention also relates to the use at least one binding agent which binds to a biomarker selected from the group consisting of a BNP-type peptide, IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a sample of a subject who suffers from (i) abnormal MFS, and/or (ii) LVH for predicting the risk of the subject of rapidly progressing to chronic heart failure and/or of hospitalization due to chronic heart failure and/or death.

All references referred to above are herewith incorporated by reference with respect to their entire disclosure content as well as their specific disclosure content explicitly referred to in the above description.

EXAMPLES

The following Examples shall illustrate the invention. They shall, however, not be construed as limiting the scope of the invention.

Example 1

The combination of several circulating biomarkers with abnormal midwall fractional shortening (MFS), an early echocardiographic indicator of preclinical systolic dysfunction, with adverse outcome was investigated.

Circulating levels of various biomarkers (NTproBNP, ICAM1, cTNT, FGF23, IGFBP7, MMP2, PLGF, eSelectin, GDF15, ST2, Galectin-3, Vitamin D, CRP, CystatineC, OPN, P1NP, Mimecan, Endostatin, proANP, ANG2) were measured in 550 elderly individuals (age 65-84 years) selected from the in PREDICTOR study. Participants were referred to cardiology centers for clinical examination and comprehensive Doppler echocardiography with centrally-measured MFS. Absolute numbers of all cause death were available after a median follow-up of 46 [39-54] months from record-linkage of administrative data. Death was recorded in 36 cases.

Individuals with LV midwall dysfunction (MFS<15%) had higher levels of NT-proBNP, cTnT, IGFBP7, sST2, GDF15, ICAM1 or FGF23 than those with normal function. The relative incidence of mortality among individuals with abnormal MFS and elevated NT-proBNP (>75th age- and sex-specific percentile) was 14.29% vs. 1.96% (abnormal MFS, low NT-proBNP), 6.22% (normal MFS, high NT-proBNP) and 0.85% (normal MFS, low NT-proBNP) (FIG. 1).

Figure 2:
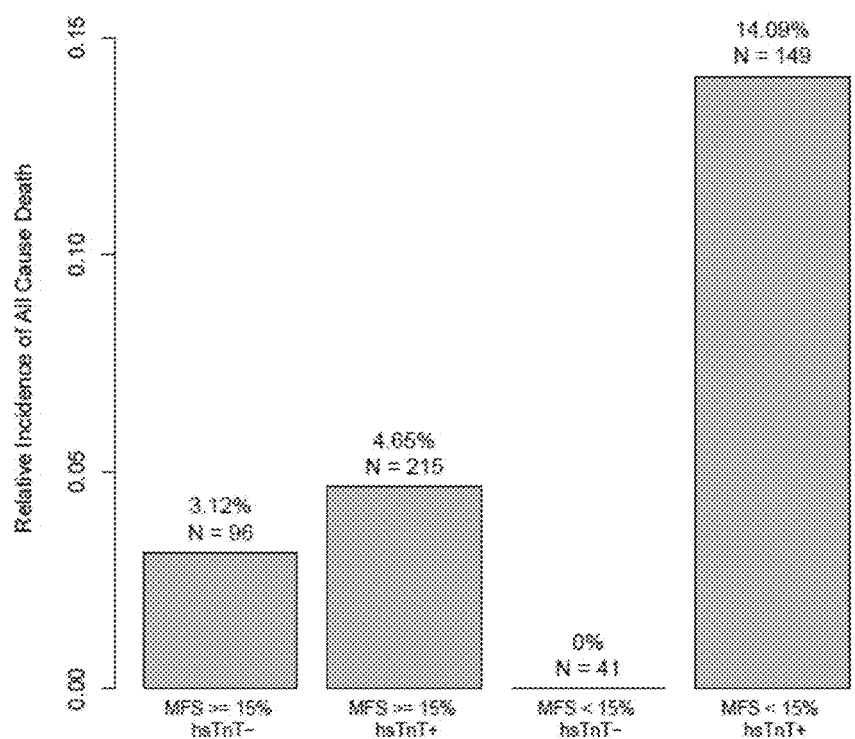
FIG. 2 Incidence for death stratified according to biomarker group (cTnT MFS) in all patients.
Figure 3:
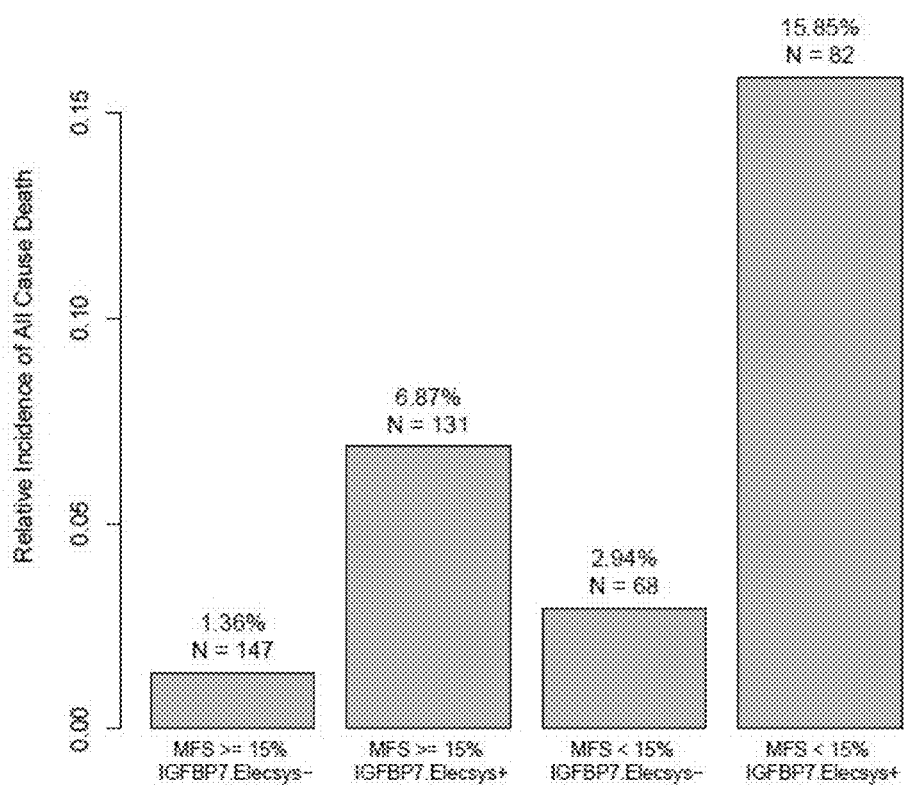
FIG. 3 Incidence for death stratified according to biomarker group (IGFBP7, MFS) in all patients.
Figure 4:
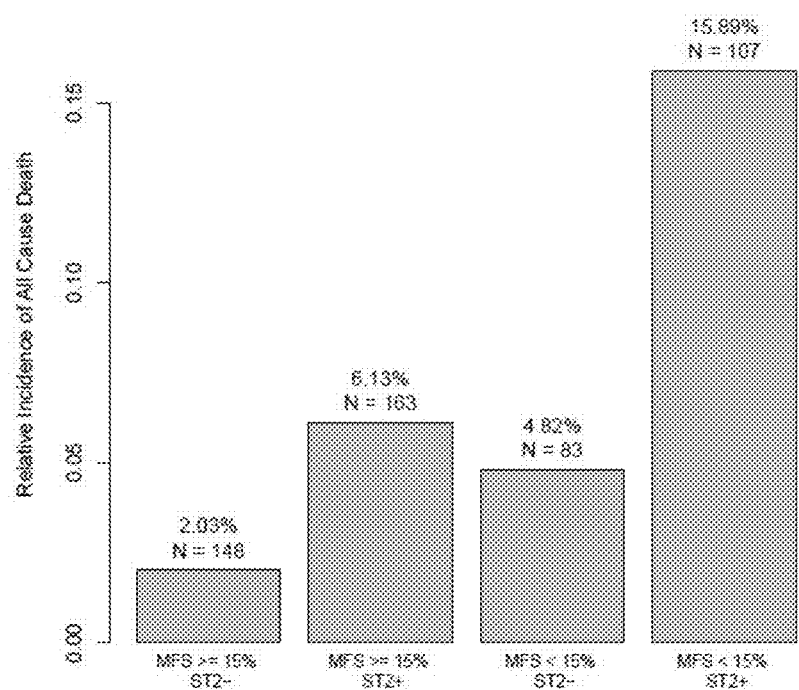
FIG. 4 Incidence for death stratified according to biomarker group (sST2, MFS) in all patients.
Figure 5:
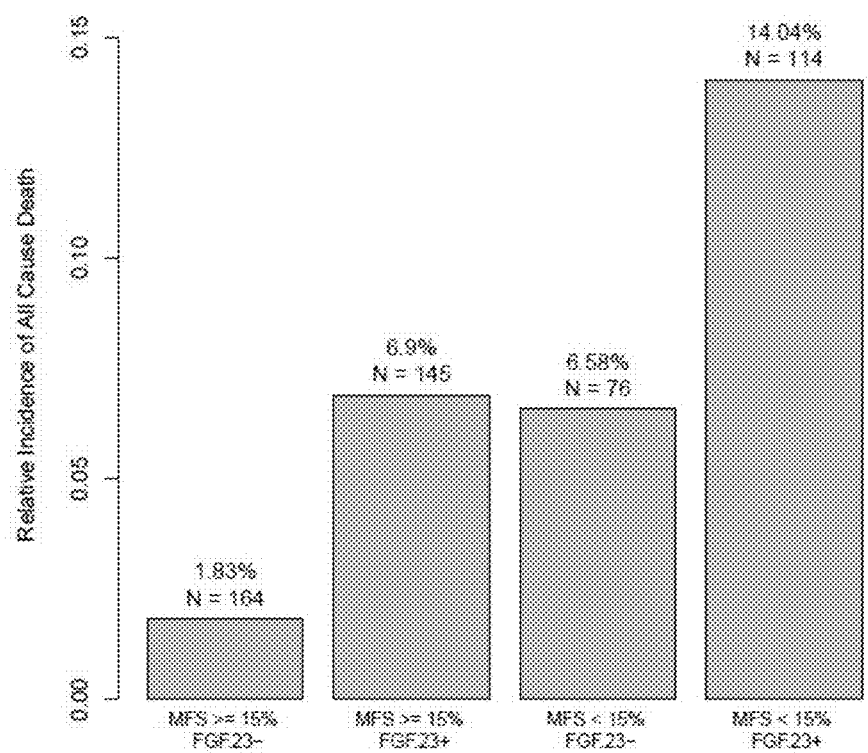
FIG. 5 Incidence for death stratified according to biomarker group (FGF23, MFS) in all patients.

Corresponding values for cTnT (>3 ng/L) were 14.09, 0.0, 4.65 and 3% (FIG. 2). Corresponding values for IGFBP7 above median concentration were 15.85, 2.94, 6.87 and 1.36% (FIG. 3). Corresponding values for sST2 above median concentration were 15.89 4.82, 6.13 and 2.03% (FIG. 4). Corresponding values for FGF23 above median concentration were 14.04, 6.58, 6.9 and 1.83% (FIG. 5).

After adjustment for sex, age, eGFR and history of hypertension, subjects with abnormal MFS and elevated NTproBNP, IGFBP7, FGF23, GDF15, ICAM1, ANG2 or sST2 had a higher risk of mortality compared to those with normal MFS and low NT proBNP, IGFBP7, FGF23, GDF15, ICAM1, ANG2 or sST2.

Hazard Ratio (HR)=11.4 for NTproBNP (p=0.002), HR=6.1 for ST2 (p=0.005), HR=7.4 (p=0.002) for ICAM1, HR=3.2 (p=0.02) for Angiopoietin2, HR=6.5 (p=0.002) for IGFBP7, HR=7.46 (p=0.002) for FGF23, HR=7.39 (p=0.002) for GDF15 (Table 1).

Elevation in of circulating NTproBNP, cTnT, IGFBP7, FGF23, GDF15, ICAM1, ANG2 or sST2 combined with early alterations in LV systolic function with MFS identify a subgroup of individuals in the general population aged 65 or more at higher risk for death.

After adjustment for sex, age, eGFR and history of hypertension, subjects with abnormal MFS and elevated NTproBNP in combination with elevated ST2 or IGFBP7 or GDF15 or FGF23 had a higher risk of mortality compared with those with normal MFS and low NTproBNP, ST2, FGF23, GDF15, IGFBP7. HR=20.01 for NTproBNP and IGFBP7, HR=19.07 for NTproBNP and ST2, 10.54 for NTproBNP and FGF23, HR=12.62 for NTproBNP and GDF15 (Table 1). After adjustment for sex, age, eGFR and history of hypertension, subjects with abnormal MFS and elevated IGFBP7 in combination with elevated ST2 had a higher risk of mortality compared with those with normal MFS and low IGFBP7 and low ST2. HR=17.96 for IGFBP7 and ST2 (Table 1).

Elevated circulating NTproBNP showed the most pronounce association to adverse outcome when measured combined with abnormal MFS (Table 1). Elevated circulating NTproBNP showed the most pronounced association to adverse outcome/mortality when measured in combination with elevated circulating IGFBP7 and either abnormal MFS or LVH (FIGS. 11 and 12, Table 1).

After adjustment for sex age eGFR and history of hypertension in subjects with abnormal MFS and elevated NTproBNP, Ang2, ICAM1, IGFBP7, sST2, GDF15 and FGF23 were found to have a significant higher risk for mortality (Table 1).

In contrast several other biomarkers included in the present investigation were not found to be suited when measured combined with abnormal MFS to identify a subgroup in the elderly population at higher risk for CV/HF related adverse outcome.

Elevated CRP, CysC, Vitamin D and proANP were not found to be pronounced associated with higher risk of death in subjects with abnormal MFS. After adjustment for sex, age, egFR and history of hypertension in subjects with abnormal MFS and elevated CRP, CysC, proANP VitaminD were not found to have significant higher risk for mortality compared to those with no abnormal MFS and low respective biomarker levels (Table 1).

Example 2

The combination of the biomarkers referred to in Example 1 with abnormal MFS was investigated further in a subset of samples derived from participants of the PREDICTOR study with normal left ventricular mass.

Figure 6:
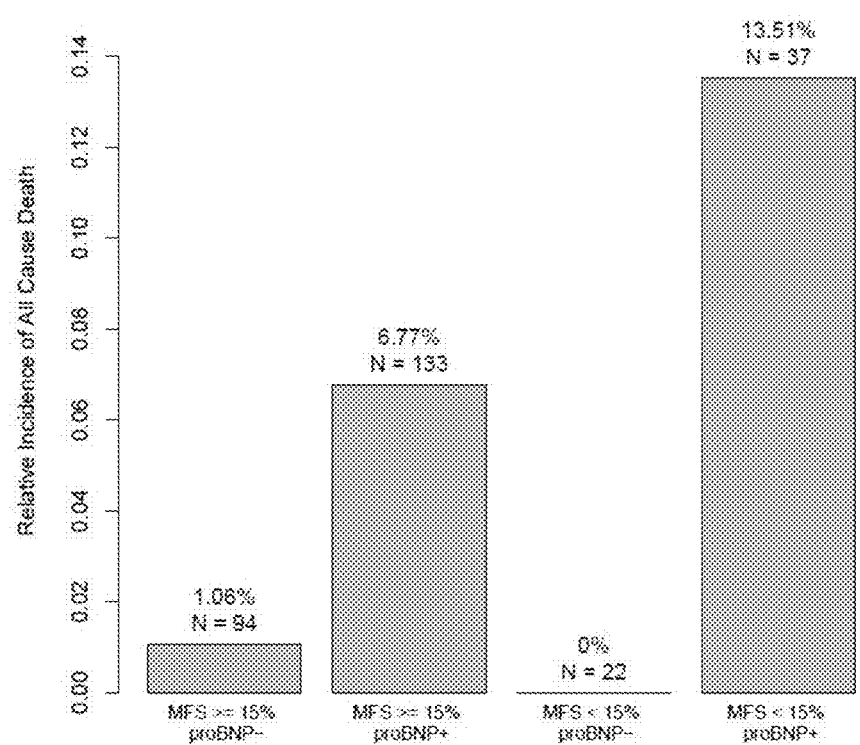
FIG. 6 Incidence for death stratified according to biomarker group (NTproBNP MFS) in patients with normal LV mass.
Figure 8:
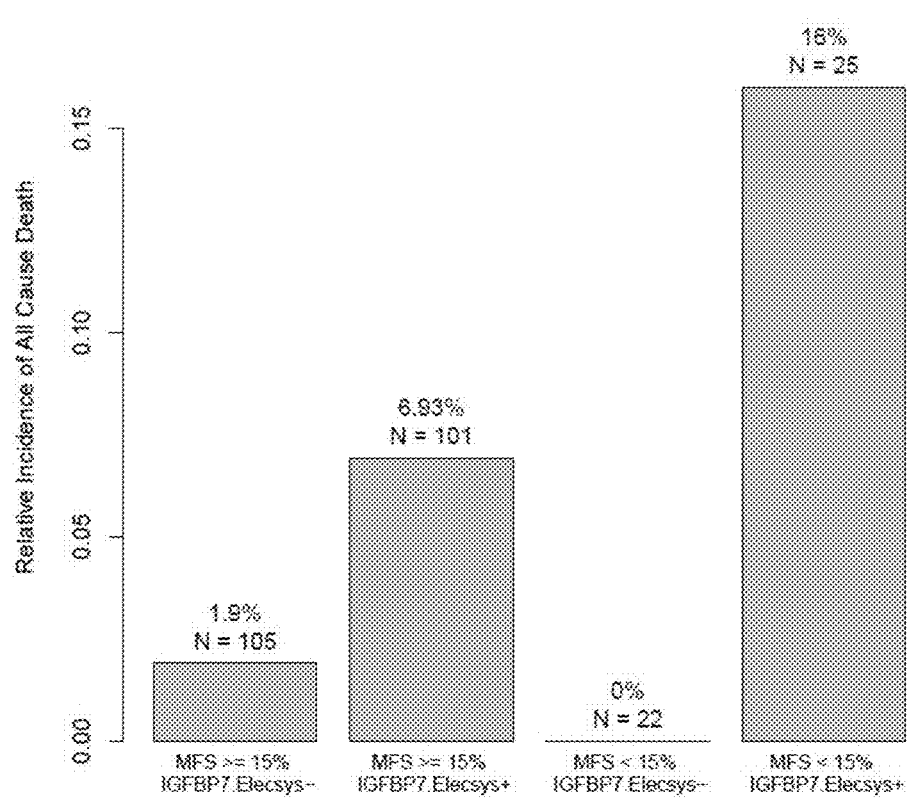
FIG. 8 Incidence for death stratified according to biomarker group (IGFBP7, MFS) in patients with normal LV mass.

Individuals with LV midwall dysfunction (MFS<15%) had higher levels of NT-proBNP, cTnT, IGFBP7, sST2 or FGF23 than those with normal function. The relative incidence of mortality among individuals with abnormal MFS and elevated NT-proBNP (>75th age- and sex-specific percentile) was 13.51% vs. 0% (abnormal MFS, low NT-proBNP), 6.77% (normal MFS, high NT-proBNP) and 1.06% (normal MFS, low NT-proBNP) (FIG. 6). Corresponding values for IGFBP7 above median concentration were 16, 0%, 6.93% and 1.9% (FIG. 8).

Figure 7:
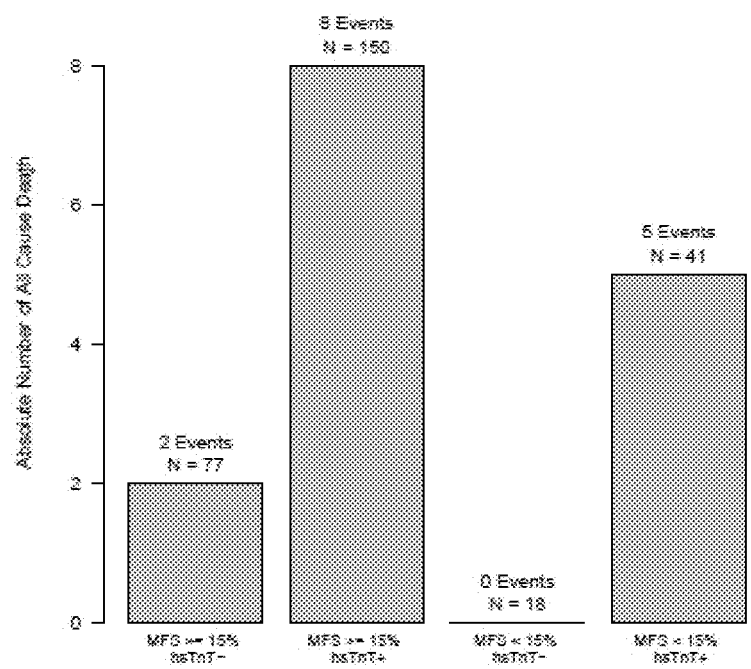
FIG. 7 Incidence for death stratified according to biomarker group (cTnT, MFS) in patients with normal LV mass.
Figure 9:
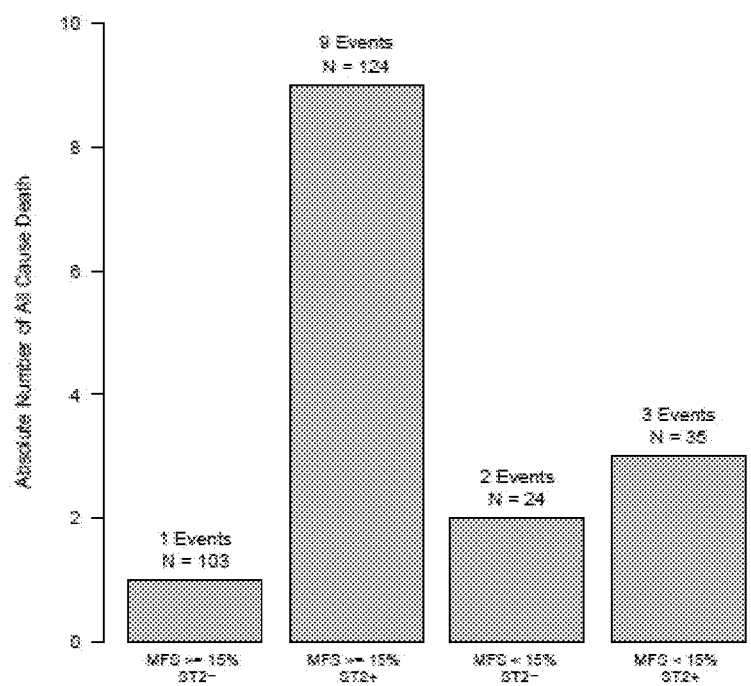
FIG. 9 Incidence for death stratified according to biomarker group (sST2, MFS) in patients with normal LV mass.
Figure 10:
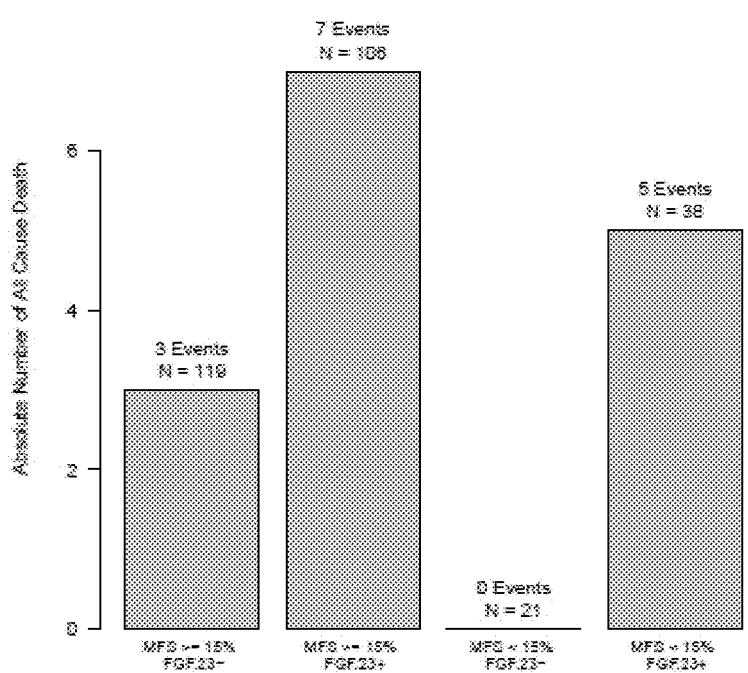
FIG. 10 Incidence for death stratified according to biomarker group (FGF23, MFS) in patients with normal LV mass.

Absolute numbers of death among individuals with abnormal MFS and elevated cTnT (>3 ng/L) were 5 vs. 0 (abnormal MFS, low cTnT), 8 (normal MFS, high cTnT) and 2 (normal MFS, low cTnT)(FIG. 7). Corresponding numbers for sST2 above median concentration were 3.2, 9 and 1. Corresponding numbers for FGF23 above median concentration were 5, 0, 7 and 3. (FIG. 9) (FIG. 10).

Elevation in of circulating NTproBNP, cTnT, IGFBP7, FGF23 or sST2 combined with early alterations in LV systolic function with MFS identify a subgroup of individuals in the general population aged 65 or more with normal left ventricular mass at higher risk for CV/HF related hospitalization/death and/or all cause death.

In contrast several other biomarkers included in the present investigation were not found to be suited when measured combined with abnormal MFS in subjects with normal LV mass to identify a subgroup in the elderly population at higher risk for CV/HF related adverse outcome.

Example 3

The combination of several circulating biomarkers with left ventricular hypertrophy, an early echocardiographic indicator of preclinical structural heart disease, with adverse outcome was investigated.

Circulating levels of NT-proBNP, ICAM-1, ST2, hsCRP, CystatinC, proANP, VitaminD, FGF23, GDF15 and IGFBP7 were measured in 550 elderly individuals (age 65-84 years) selected from the in PREDICTOR study. Absolute numbers of death were available after a median follow-up of 46 [39-54] months from record-linkage of administrative data. death was recorded in 36 cases.

Individuals with LVH had higher levels of NT-proBNP and IGFBP7, or than those with normal function. The relative incidence of mortality among individuals with LVH, elevated NTproBNP (>75$^{th}$ age and sex specific percentiles) and elevated IGFBP7 (above median concentration) was 19.15% vs. 0% (LVH, low NTproBNP, low IGFBP7), 13.79% (no LVH, high NTproBNP, high IGFBP7) and 1.08% (no LVH, low NTproBNP, low IGFBP7) (FIG. 11). The relative incidence of mortality among individuals with abnormal MFS, elevated NTproBNP (>75$^{th}$ age and sex specific percentiles) and elevated IGFBP7 (above median concentration) was 17% vs. 3% (no abnormal MFS, low NTproBNP, low IGFBP7).

Elevation in of circulating NTproBNP and IGFBP7 combined with LVH identify a subgroup of individuals in the general population aged 65 or more at higher risk for death.

Elevation of both circulating NTproBNP and IGFBP7 combined with LVH identify a subgroup of individuals in the general population aged 65 or more at higher risk for death.

After adjustment for sex, age, eGFR and history of hypertension, subjects with LVH and elevated NTproBNP and IGFBP7, had a higher risk of CV/HF related hospitalization/mortality compared to those with no LVH and low IGFBP7, NT proBNP.

Elevation of circulating NTproBNP, IGFBP-7, ICAM-1, FGF23, GDF15 or sST2 combined with LVH identify a subgroup of individuals in the general population aged 65 or more at higher risk for CV/HF related hospitalization/death and/or all cause death.

After adjustment for sex, age, eGFR and history of hypertension, subjects with LVH and elevated FGF23, GDF15, ICAM1, or sST2 had a higher risk of mortality compared to those with normal LV mass and low FGF23, GDF15, ICAM1 or sST2.

Hazard Ratio (HR)=3.5 for ST2 (p=0.08), HR=5.5 (p=0.009) for ICAM1, HR=4.9 (p=0.01) for FGF23, HR=5.83 (p=0.03) for GDF15 (Table 2).

After adjustment for sex, age, eGFR and history of hypertension, subjects with LVH and elevated NTproBNP in combination with elevated ST2 or IGFBP7 or GDF15 or FGF23 had a higher risk of mortality compared with those with normal LV mass and low NTproBNP, ST2, FGF23, GDF15, IGFBP7. HR=9.8 for NTproBNP and IGFBP7, HR=11.9 for NTproBNP and ST2, HR=8.3 for NTproBNP and FGF23, HR=7.1 for NTproBNP and GDF15 (Table 2). After adjustment for sex, age, eGFR and history of hypertension, subjects with LVH and elevated IGFBP7 in combination with elevated ST2 had a higher risk of mortality compared with those with normal MFS and low IGFBP7 and low ST2. HR=5.7 for IGFBP7 and ST2 (Table 2).

In contrast several other biomarkers included in the present investigation were not found to be suited when measured in subjects with LVH to identify a subgroup in the elderly population at higher risk for CV/HF related adverse outcome.

Elevated CRP, CysC, Vitamin D and proANP were not found to be pronounced associated with higher risk of death in subjects with LVH. After adjustment for sex, age, egFR and history of hypertension in subjects with LVH and elevated CRP, CysC, proANP VitaminD were not found to have significant higher risk for mortality compared to those with no LVH and low respective biomarker levels (Table 2).

TABLE 1

Multivariable Cox models for mortality in subjects with abnormal MFS and elevated concentrations of biomarkers

| Abnormal MFS and elevated biomarker | HR [95% CI] | P covariates: sex, age, eGFR and history of hypertension |
|---|---|---|
| ICAM-1 | 7.4 | 0.002 |
| ST2 | 6.1 | 0.005 |
| NT-proBNP | 11.4 | 0.02 |
| ANG-2 | 3.2 | 0.02 |
| IGFBP7 | 6.5 | 0.02 |
| hsCRP | 1.1 | 0.84 |
| Cystatin C | 1.54 | 0.37 |
| proANP | 1.15 | 0.75 |
| Vitamin D | 2.2 | 0.13 |
| FGF23 | 7.46 | 0.0017 |
| GDF15 | 7.39 | 0.002 |
| NTproBNP + IGFBP7 | 20.01 | 0.003 |
| NTproBNP + ST2 | 19.07 | 0.005 |
| NTproBNP + FGF23 | 10.54 | 0.025 |
| NTproBNP + GDF15 | 12.62 | 0.016 |
| IGFBP7 + ST2 | 17.96 | 0.006 |

TABLE 2

Multivariable Cox models for mortality in subjects with LVH and elevated concentrations of biomarkers

| LVH and elevated biomarker | HR [95% CI] | P covariates: sex, age, eGFR and history of hypertension |
|---|---|---|
| ICAM-1 | 5.5 | 0.009 |
| ST2 | 3.53 | 0.08 |
| NT-proBNP | 7.6 | 0.05 |
| hsCRP | 1.0 | 0.9 |
| Cystatin C | 0.98 | 0.97 |
| proANP | 0.7 | 0.5 |
| Vitamin D | 1.1 | 0.8 |
| FGF23 | 4.9 | 0.01 |
| GDF15 | 5.83 | 0.03 |
| NTproBNP + IGFBP7 | 9.8 | 0.03 |
| NTproBNP + ST2 | 11.9 | 0.02 |
| NTproBNP + FGF23 | 8.3 | 0.04 |
| NTproBNP + GDF15 | 7.1 | 0.06 |
| IGFBP7 + ST2 | 5.7 | 0.04 |

TABLE 3

Reference levels used in all investigations relating to elevated biomarkers in combination with LVH or abnormal MFS and a death

| | | Elevated concentration >75th age- and sex-specific percentiles, | | |
|---|---|---|---|---|
| Biomarker | | <40 Years | 40-50 Years | >50 Years |
| NT-proBNP (pg/mL) | Female | 63.6 | 63.4 | 73.2 |
| | Male | 25.2 | 29.9 | 45.7 |
| hsCRP (mg/L) | | >median concentration (1.63) | | |
| CysC (mg/L) | | >median concentration (1.09) | | |
| VitaminD (ng/mL) | | >median concentration (9.57) | | |
| IGFBP7 (ng/mL) | | >median concentration (171.9) | | |
| sST2 (ng/mL) | | >median concentration (15) | | |
| GDF15 (ng/L) | | >median concentration (1646) | | |

TABLE 3-continued

Reference levels used in all investigations relating to elevated biomarkers in combination with LVH or abnormal MFS and a death

| FGF23 (RU/mL) | >median concentration (76.27) |
| hs-cTnT (pg/mL) | >3 |
| ICAM1 (ng/mL) | >median concentration (218) |
| ANG2 (ng/mL) | >median concentration (1.93) |

The invention claimed is:

1. A method for predicting the risk of a human subject of progressing to chronic heart failure and/or of hospitalization due to chronic heart failure and/or of death, said method comprising:
   (a) detecting in said human subject the presence of abnormal midwall fractional shortening (abnormal MFS) using echocardiography,
   (b) measuring the level of at least one biomarker from a blood, serum or plasma sample of the human subject, said biomarker(s) selected from the group consisting of B-type natriuretic peptide (BNP) or N-terminal pro B-type natriuretic peptide (NT-proBNP), IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1) and Angiopoietin-2 (ANG2) in a sample from the subject,
   (c) comparing the level of said at least one biomarker to a reference level, and
   (d) predicting the risk of a subject of progressing to chronic heart failure and/or of hospitalization due to chronic heart failure and/or of death
wherein said subject does not suffer from left ventricular hypertrophy, and
wherein a level of the at least one biomarker above the reference level indicates that the subject is at risk of progressing to chronic heart failure and/or of hospitalization due to chronic heart failure and/or of death, or wherein a level of the at least one biomarker below the reference level indicates that the subject is not at risk of progressing to chronic heart failure and/or of hospitalization due to chronic heart failure and/or of death.

2. The method of claim 1, wherein said subject does not show symptoms of heart failure.

3. The method of claim 1, wherein said subject suffers from heart failure classified as stage A or stage B according to ACC/AHA classification.

4. The method of claim 1, wherein said subject is age 65 years or older.

5. The method of claim 1, wherein the cardiac Troponin is Troponin T or Troponin I.

6. The method of claim 1, wherein the risk of a subject of progressing to chronic heart failure and/or of hospitalization due to chronic heart failure and/or of death within a window period of 3 years is predicted.

7. The method of claim 1, wherein the at least one biomarker is selected from the group consisting of a B-type natriuretic peptide (BNP) or N-terminal pro B-type natriuretic peptide (NT-proBNP), sST2, IGFBP7, a cardiac Troponin and FGF23.

8. A method for predicting the risk of a human subject of progressing to chronic heart failure and/or of hospitalization due to chronic heart failure and/or of death, said method comprising:
   (a) measuring the blood, serum or plasma level from the human subject of at least one biomarker selected from the group consisting of a B-type natriuretic peptide (BNP) or N-terminal pro B-type natriuretic peptide (NT-proBNP), IGFBP7 (IGF binding protein 7), a cardiac Troponin, soluble ST2 (sST2), FGF-23 (Fibroblast Growth Factor 23), Growth Differentiation Factor 15 (GDF-15), Intercellular Adhesion Molecule 1 (ICAM-1), and Angiopoietin-2 (ANG2) in a serum or plasma sample from a subject who suffers from abnormal MFS,
   (b) comparing the level of said at least one biomarker to a reference level, wherein said subject does not suffer from left ventricular hypertrophy; and
   (c) predicting the risk of a subject of progressing to chronic heart failure and/or of hospitalization due to chronic heart failure and/or of death, and
   (d) administering a medicament selected from the group consisting of an angiotensin-converting enzyme (ACE) inhibitors, an angiotensin receptor antagonist (ARB), an aldosterone antagonist, a diuretic and a beta blocker,
wherein a level of the at least one biomarker above the reference level indicates that the subject is at risk of progressing to chronic heart failure and/or of hospitalization due to chronic heart failure and/or of death, or wherein a level of the at least one biomarker below the reference level indicates that the subject is not at risk of progressing to chronic heart failure and/or of hospitalization due to chronic heart failure and/or of death.

9. The method of claim 8, wherein the risk of a subject progressing to chronic heart failure and/or of hospitalization due to chronic heart failure and/or of death within a window period of 3 years is predicted.

10. The method of claim 1, wherein the levels of B-type natriuretic peptide (BNP) or N-terminal pro B-type natriuretic peptide (NT-proBNP) and IGFBP7 are measured.

11. The method of claim 8, wherein the levels of B-type natriuretic peptide (BNP) or N-terminal pro B-type natriuretic peptide (NT-proBNP) and IGFBP7 are measured.

12. The method of claim 1 wherein the selected biomarker is BNP or NT-proBNP.

13. The method of claim 1 wherein the selected biomarker is a cardiac Troponin.

14. The method of claim 1 wherein the selected biomarker is soluble ST2.

15. The method of claim 1 wherein the selected biomarker is FGF-23.

16. The method of claim 1 wherein the selected biomarker is GDF-15.

17. The method of claim 1 wherein the selected biomarker is ICAM-1.

18. The method of claim 1 wherein the selected biomarker is IGFBP7.

19. The method of claim 1 wherein the selected biomarker is ANG2.

20. The method of claim 1 wherein the detection in step (a) comprises obtaining echocardiographic images of the heart from the subject to be tested.

21. The method of claim 20 wherein the images are obtained by M-mode echocardiography, 2D speckle tracking echocardiography, Doppler echocardiography, or two-dimensional echocardiography.

22. The method of claim 1, wherein step (b) comprised the measurement of the level of the at least one biomarker in a sample from a subject in which the presence of abnormal MFS was detected.

23. The method of claim 8 wherein the levels of at least two of the biomarkers in step (a) are measured.

* * * * *